US00PP09621P

United States Patent [19]

Lamb

[11] Patent Number: Plant 9,621

[45] Date of Patent: Aug. 6, 1996

[54] CALATHEA PLANT NAMED ECLIPSE

[75] Inventor: Ann E. Lamb, Sebring, Fla.

[73] Assignee: Twyford International Inc., Santa Paula, Calif.

[21] Appl. No.: 434,367

[22] Filed: May 3, 1995

[51] Int. Cl.[6] ..... A01H 5/00

[52] U.S. Cl. ..... Plt./88.1

[58] Field of Search ..... Plt./88.1

[56] References Cited

U.S. PATENT DOCUMENTS

P.P. 8,836 7/1994 Lamb ..... Plt./88.1

*Primary Examiner*—James R. Feyrer
*Attorney, Agent, or Firm*—Foley & Lardner

[57] ABSTRACT

A Calathea plant named 'Eclipse' having dark green round leaves bordered with a distinctive broad metallic silver-green band which is often variably tinged with pink.

1 Drawing Sheet

The present invention comprises a new and distinct cultivar of Calathea, botanically known as *Calathea roseo picta,* and referred to by the cultivar name 'Eclipse'.

The new cultivar is a mutation discovered by the inventor Ann E. Lamb in Apopka, Fla. The cultivar was discovered and selected by the inventor from tissue culture derived plants of an unnamed parent of *C. roseo picta* in Apopka, Fla., in December 1993. Propagation by tissue culture and division by the inventor in Apopka, Fla. was used to increase the number of plants for evaluation and has demonstrated the stability of the combination of characteristics from generation to generation.

The following observations, measurements and values describe plants grown in Apopka, Fla. under greenhouse conditions which closely approximate those generally used in horticultural practice.

The following traits have been repeatedly observed to be characteristics which in combination distinguish 'Eclipse' from other plants of the species *C. roseo picta,* and from the patented cultivar 'Rosy', disclosed in U.S. Plant Pat. No. 8,836.

1. The plant, particularly when juvenile, produces leaves having an unusually broad marginal band of metallic silver-green tinged with pink which extends nearly to the leaf edge which is dark green.

2. The center of the leaf is very dark green; the midrib is silver-green tinged with pink.

3. As the plant matures, the broad silver-green marginal bands become diffuse on their borders, and the leaf develops a broader dark green edge.

4. As the plant matures, the quantity and intensity of the pink markings diminishes.

5. The leaf color pattern of 'Eclipse' is opposite that of 'Rosy'.

All color references are measured against The Royal Horticultural Society color chart. Colors are approximate as color depends on horicultural practices such as light level and fertilization rate, among others, without, however, any variance in genotype.

The color photographic drawing comprises a top perspective view of a plant of 'Eclipse' in a 15.5 cm pot approximately 16 weeks after planting a 16-week-old liner obtained by tissue culture and grown under appropriate growing conditions. Colors are as accurate as possible with color illustrations of this type.

Origin: Mutation of *Calathea roseo picta.*

Classification: *Calathea roseo picta,* cv, 'Eclipse'.

Propagation: Asexual propagation either by tissue culture or division.

Plant: In a 15.5 cm pot for a plant grown from a 16-week-old liner after 16 weeks under appropriate growing conditions, 'Eclipse' is approximately 10–13 cm in height and approximately 18–21 cm in width.

*Leaves.*—Form: The leaf blade is orbicular with a mucronate tip and an obtuse base. The margins are entire. The midrib tends to be straight or curved upward slightly over the length of the leaf. The leaf blade is wavy over the width of the leaf. Size: Leaf blades are approximately 9.2–10.5 cm in length and approximately 8.6–9.4 cm in width. Petiole: The petiole is approximately 5.9–5.0 cm in height from the base of the petiole to the base of the leaf blade on the primary shoot. Secondary shoots are somewhat smaller depending on the age of the shoot. The petiole is approximately 4 mm in diameter just below the geniculum. The petiole below the geniculum is straight. Petiole wings: Petiole wings are approximately 4.8 cm in length and approximately 6 mm in width at their midpoint. The tip of the petiole wings is rounded. There is approximately 2–6 mm between the top of the wing and the base of the geniculum. Geniculum: The geniculum is approximately 9 mm in length, and approximately 4 mm in diameter. The color is greener than but closest to 177 A. There is no space between the top of the geniculum and the base of the leaf blade. The geniculum is prominent. The orientation of the leaf to the petiole is variable, as the geniculum bends. During the night and early morning, the geniculum is straight, and the leaf is held nearly vertical above the petiole. During the day, the geniculum is bent, and the leaf is oriented approximately 90 degrees to the petiole. Veins: Veins and midrib are sunken, with the leaf blade slightly concave between veins on the upper surface. The midrib protrudes from the lower surface. Primary veins on leaves radiate out from the midrib along the length of the leaf. Veins are recessed within the leaf. There are approximately 12–14 primary veins on the leaf.

*Color pattern.*—The upper leaf surface is very dark green in the center, with broad marginal silver-green bands, often variably tinged with pink. The leaf midrib is silver-green tinged with pink. The marginal silver-green bands extend nearly to the leaf edge on juvenile plants. However, as the plant matures, the silver bands become somewhat diffuse on their borders and the leaf develops a dark green edge. The quantity and intensity of the pink markings diminishes as the plant matures. Upper surface color: Margin: Metallic 194 B with flecks of 58 A. Leaf center: Darker and greener than, but closest to, 139 A. Midrib: Upper surface 59 D, outlined with metallic 194 D. Lower surface color: Entirely 187 A. Midrib: Greener and redder than, but closest to, 177 A. Petiole: Anthocyanous 187 A. Petiole wing: Lighter than, but closest to, 187 A.

Inflorescence: The inflorescence of 'Eclipse' is typical of the species *Calathea roseo picta* and has no commercial significance.

Roots: Dark brown fibrous roots with fine laterals.

General observation: A new and distinctive Calathea named 'Eclipse' having very dark green round leaves bordered with a distinctive broad silver-green band, which is variably tinged with pink. The leaf midrib is pink and silver-green. These combined characteristics make Calathea 'Eclipse' a unique new cultivar.

It is claimed:

1. A new and distinct cultivar of Calathea plant named 'Eclipse', as illustrated and described.

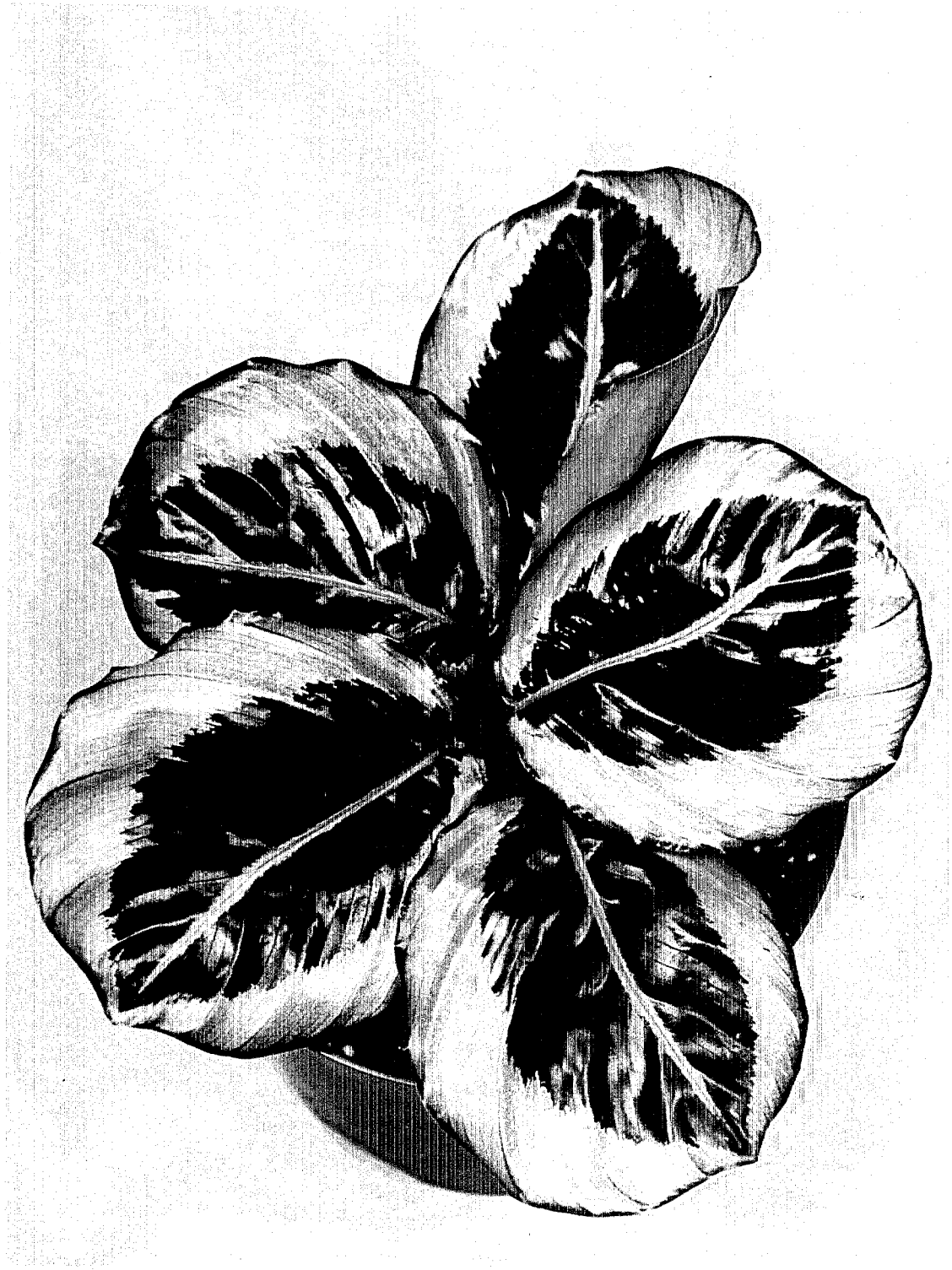

* * * * *